US012656436B2

(12) United States Patent
Speidel et al.

(10) Patent No.: US 12,656,436 B2
(45) Date of Patent: Jun. 16, 2026

(54) SYSTEM AND METHOD FOR ACQUISITION OF A MAGNETIC RESONANCE IMAGE AS WELL AS DEVICE FOR DETERMINING A TRAJECTORY FOR ACQUISITION OF A MAGNETIC RESONANCE IMAGE

(71) Applicant: Universitaet Ulm, Ulm (DE)

(72) Inventors: Tobias Speidel, Ulm (DE); Volker Rasche, Erbach (DE)

(73) Assignee: Universitaet Ulm, Ulm (DE)

( * ) Notice: Subject to any disclaimer, the term of this patent is extended or adjusted under 35 U.S.C. 154(b) by 357 days.

(21) Appl. No.: 18/240,038

(22) Filed: Aug. 30, 2023

(65) Prior Publication Data

US 2023/0408614 A1 Dec. 21, 2023

Related U.S. Application Data

(63) Continuation of application No. PCT/EP2022/055348, filed on Mar. 3, 2022.

(30) Foreign Application Priority Data

Mar. 4, 2021 (EP) .................................... 21160759

(51) Int. Cl.
 *G01R 33/56* (2006.01)
 *G01R 33/48* (2006.01)
 (Continued)

(52) U.S. Cl.
 CPC ..... *G01R 33/5608* (2013.01); *G01R 33/4822* (2013.01); *G06T 15/205* (2013.01);
 (Continued)

(58) Field of Classification Search
 None
 See application file for complete search history.

(56) References Cited

U.S. PATENT DOCUMENTS

2002/0143247 A1* 10/2002 Brittain ............ G01R 33/56375
                                                        600/410
2011/0142315 A1* 6/2011 Hsieh ..................... A61B 6/037
                                                        382/131

(Continued)

OTHER PUBLICATIONS

International Search Report and Written Opinion from International Application No. PCT/EP2022/055348 dated May 23, 2022.

(Continued)

*Primary Examiner* — Nasima Monsur
(74) *Attorney, Agent, or Firm* — MARSHALL, GERSTEIN & BORUN LLP

(57) ABSTRACT

The present invention relates to a method for acquisition of a magnetic resonance image independent on an a-priori defined field-of-view (FOV), the method comprising the sequence of steps: determining a k-space trajectory for acquisition of k-space MRI data, wherein said k-space trajectory comprises a field-of-view, FOV, independent 3D k-space trajectory, wherein the 3D k-space trajectory for acquisition of the k-space MRI data is independent of an a-priori defined field-of-view of an MRI image to be constructed, in particular wherein said field-of-view-independent 3D k-space trajectory is based on one or more Jacobi theta functions; acquiring k-space MRI data, wherein a gradient waveform corresponding to said field-of-view independent k-space trajectory is applied to magnetic field gradients of the MRI scanner; and selecting a desired field of view for the magnetic resonance image after acquiring the k-space MRI data and constructing the magnetic resonance image based on the desired field of view from the acquired k-space MRI data.

13 Claims, 9 Drawing Sheets

(51) Int. Cl.
    G06T 15/20       (2011.01)
    G16H 30/40       (2018.01)

(52) U.S. Cl.
    CPC ......... G16H 30/40 (2018.01); *G06T 2200/24*
                (2013.01); *G06T 2210/41* (2013.01)

(56)              References Cited

U.S. PATENT DOCUMENTS

| | | | |
|---|---|---|---|
| 2012/0098539 A1* | 4/2012 | Sakellariou | ........ G01R 33/3808 |
| | | | 324/318 |
| 2014/0005520 A1* | 1/2014 | Foo | ...................... G01R 33/481 |
| | | | 600/411 |

OTHER PUBLICATIONS

Scheffler et al., "Frequency Resolved Single-Shot MR Imaging Using Stochastic k-Space Trajectories," MRM 35:569-576 (1996).

Search Report from European Application No. 21160759.3 dated Aug. 25, 2021.

Speidel et al., "Efficient 3D Low-Discrepancy k-Space Sampling Using Highly Adaptable Seiffert Spirals," IEEE Transactions on Medical Imaging, 38(8):1833-1840 (2019).

Speidel et al., "On the possibility of reconstructing arbitrary FOVs using theta function based gradient waveforms with low-coherent aliasing properties," In: "Low-Discrepancy k-Space Sampling Strategies for Magnetic Resonance Imaging," Universität Ulm, Internet, 12 pages (2021).

Ye et al., "Fast MR Image Reconstruction for Partially Parallel Imaging With Arbitrary κ-Space Trajectories," IEEE Transactions on Medical Imaging, 30(3):575-585 (2011).

* cited by examiner a)

b)

$$\Delta r = \sqrt{\overline{x_i}^2 + \overline{y_i}^2}$$

SYSTEM AND METHOD FOR ACQUISITION OF A MAGNETIC RESONANCE IMAGE AS WELL AS DEVICE FOR DETERMINING A TRAJECTORY FOR ACQUISITION OF A MAGNETIC RESONANCE IMAGE

CROSS-REFERENCE TO RELATED APPLICATIONS

This is a Continuation application of International patent application PCT/EP2022/055348, filed 3 Mar. 2022 and designating the United States, which was published as WO 2022/184808 A1, and claims the priority of European patent application 21 160 759.3, filed 4 Mar. 2021, which are incorporated herein by reference in their entireties.

FIELD OF THE INVENTION

The present disclosure relates to the field of medical imaging, in particular to a method for acquisition of a magnetic resonance image using an MRI scanner; a device for determining a trajectory for acquisition of an MRI image, a magnetic resonance imaging (MRI) system and a computer program.

BACKGROUND OF THE INVENTION

Magnetic resonance imaging (MRI) is a medical imaging technique used in radiology to form pictures of the anatomy and the physiological processes of the body. MRI scanners use strong magnetic fields, magnetic field gradients, and radio waves to generate images of the body.

An advantage over other medical imaging modalities such as X-ray or a computed tomography, CT, scan is that MRI does not require ionizing radiation. However, a drawback of magnetic resonance imaging is the long acquisition time required for acquisition of MRI image data. In order to achieve acquisition times that are acceptable in clinical practice, the first step in any MRI acquisition method is to select only a limited field of view (FOV). For acquisition of a volumetric 3D MRI image, the measurement signal is acquired while at the same time applying up to three different gradient fields. The application of the gradients defines parameters such as the maximum volume size and the maximum resolution of the resulting MRI image. An MRI trajectory in spatial frequency space (k-space) is determined by the relationship of the individual gradient fields during acquisition and by the discrete sampling of the signal, induced in dedicated receive coils.

Exemplary MRI trajectories are disclosed in Gurney et al., "Design and Analysis of a Practical 3D Cones Trajectory," Magnetic Resonance in Medicine 55:575-582, 2006. The proposed 3D Cones k-space trajectory claims to have many desirable properties for rapid and ultra-short echo time magnetic resonance imaging. An algorithm is presented that generates the 3D Cones gradient waveforms given a desired field of view and resolution. As described in the results section of this paper, the approach disclosed therein provides a coherent aliasing pattern along the z-axis, outside the prescribed FOV, due to the 3D Cones' symmetry around that axis.

Xiaojing Ye et al., "Fast MR image reconstruction for partially parallel imaging with arbitrary k-space trajectories", IEEE transactions on medical imaging, vol. 30, no. 3, pages 575-585, 2011, discloses a fast MR image reconstruction for partially parallel imaging with arbitrary k-space trajectories. According to its abstract, both acquisition and reconstruction speed are crucial for magnetic resonance (MR) imaging in clinical applications. A fast reconstruction algorithm for SENSE in partially parallel MR imaging with arbitrary k-space trajectories shall be provided. The proposed method is a combination of variable splitting, the classical penalty technique and the optimal gradient method.

Klaus Scheffler et al., "Frequency resolved single-shot MR imaging using stochastic k-space trajectories", Magnetic Resonance in Medicine, vol. 35, no. 4, pages 569-576, 1996 discloses frequency resolved single-shot MR imaging using stochastic k-space trajectories.

The general background of MRI imaging and k-space data acquisition is described in the literature, for example in Moreneburg, "Bildgebende Systeme für die medizinische Diagnostik" (English: Imaging system for medical diagnostics), Publicis MCD Verlag, 1995 or in Dössel, "Bildgebende Verfahren in der Medizin—von der Technik zur medizinischen Anwendung" (English: Imaging methods in medicine—from technology to medical application), Springer, 2000, the contents of which are incorporated herein by reference.

BRIEF SUMMARY OF THE INVENTION

It can be among others an object of aspects the present disclosure to further improve the acquisition of MRI image data. In particular, it would be advantageous to overcome limitations in clinical practice such as overcoming the need for performing subsequent scans in case of cut-off organ parts or reducing idle times during image acquisition. Moreover, it would be desirable to provide a device and method that may help to increase patient throughput, thereby reducing the cost for MRI imaging per patient or enabling more detailed analysis.

In a first aspect of the present disclosure a method for acquisition of a magnetic resonance image independent on an a-priori defined field-of-view (FOV) is presented, the method comprising the sequence of steps:

determining a k-space trajectory for acquisition of k-space MRI data, wherein said k-space trajectory comprises a field-of-view, FOV, independent 3D k-space trajectory, wherein the 3D k-space trajectory for acquisition of the k-space MRI data is independent of an a-priori defined field-of-view of an MRI image to be constructed, acquiring k-space MRI data, wherein a gradient waveform corresponding to said field-of-view independent k-space trajectory is applied to magnetic field gradients of the MRI scanner; and selecting a desired field of view for the magnetic resonance image after acquiring the k-space MRI data and constructing the magnetic resonance image based on the desired field of view from the acquired k-space MRI data.

A second aspect refers to the use of on one or more gradient waveforms, derived from a field-of-view, FOV, independent k-space trajectory, in particular derived from Jacobi theta functions, for acquisition of MRI image data, wherein the 3D k-space trajectory for acquisition of the k-space MRI data is independent of an a-priori defined field-of-view of the MRI image. Similarly, the use of one or more Jacobi theta functions for determining a field-of-view, FOV, independent k-space trajectory for acquisition of MRI image data is provided.

In a third aspect a device for determining a trajectory for acquisition of an MRI image is presented, wherein the device is adapted to determine a k-space trajectory for acquisition of k-space MRI data independent of an a-priori defined field of view, FOV, wherein the 3D k-space trajectory for acquisition of the k-space MRI data is independent of an a-priori defined field-of-view of the MRI image, in particular wherein said k-space trajectory comprises a field-of-view independent 3D k-space trajectory based on one or more Jacobi theta functions.

In a further aspect, a magnetic resonance imaging system for acquisition of a magnetic resonance image is presented, the system comprising:

a device for determining a trajectory for acquisition of an MRI image as described above;

an MRI scanner adapted to acquire k-space MRI data, wherein a gradient waveform corresponding to said field-of-view independent k-space trajectory is applied to magnetic field gradients of the MRI scanner; and an image reconstruction device comprising an interface for selecting a desired field of view for the magnetic resonance image after acquiring the k-space MRI data, and adapted to construct the magnetic resonance image based on the desired field of view from the acquired k-space MRI data.

In yet further aspects of the present disclosure, there are provided a corresponding computer program which comprises program code means for causing a computer to determine a k-space trajectory for acquisition of k-space MRI data independent of an a-priori defined field-of-view, FOV, wherein the 3D k-space trajectory for acquisition of the k-space MRI data is independent of an a-priori defined field-of-view of the MRI image, in particular wherein said k-space trajectory comprises a field-of-view independent 3D k-space trajectory based on one or more Jacobi theta functions, as well as a non-transitory computer-readable recording medium that stores therein a computer program product as described above, which, when executed by a processor, causes the respective processing step disclosed herein to be performed.

Preferred embodiments of the disclosure are defined in the dependent claims. It shall be understood that the claimed method, use, device, system, computer program and medium have similar and/or identical preferred embodiments as the claimed system, in particular as defined in the dependent claims and as disclosed herein.

The conventional approach for reducing an MRI acquisition time is to select a small field of view so as to avoid unnecessary data acquisition. Conventional MRI k-space trajectories are thus determined based on a-priori defined field-of-view, i.e., based on the a-piori defined field-of-view of the MRI image to be constructed. The field of view of the MRI image to be constructed is usually selected by an operator prior to acquisition of the MRI data. However, a drawback is that, if the field of view is not selected properly, there is a need for subsequent acquisition of additional elements such as cut-off organ parts which often require an entirely new time-consuming MRI scan. Hence, the patient throughput may be limited leading to high cost and undesirable waiting times. In addition, the planning effort for medical personnel is rather significant with the conventional approach.

An aspect of the invention is based on the idea to acquire the magnetic resonance image independent of an a-priori defined field of view. Hence, instead of first setting the field of view and then acquiring the MRI data, it is suggested to first acquire the MRI data in particular with a specifically tailored k-space trajectory based on one or more Jacobi theta functions. This new approach allows to select a desired FOV and to (re)construct a magnetic resonance image based on a desired FOV after acquisition of the MRI data from the acquired k-space MRI data. With conventional MRI trajectories, the acquisition time for covering a large FOV may be prohibitively long. The inventors recognized that, due to its advantageous mathematical properties, using one or more Jacobi theta functions for determining a k-space trajectory allows reconstructing MRI images without prior selection of the FOV in practical applications. Alternatives to Jacobi theta functions are for example Weierstrass elliptical functions, Lemniscate elliptical functions, and/or Dixon elliptical functions. More generally speaking a k-space trajectory may be selected wherein the parametrization is adapted to be continuously differentiable, as least over a predetermined interval; the parametrization is adapted to provides a low discrepancy; and/or the parametrization is adapted to provide degrees of freedom for an iterative optimization process. Jacobi theta functions are merely one exemplary class of functions, while other functions such as the class of double-periodic functions can be used. Further to the aforementioned example Weierstrass elliptical functions, Lemniscate elliptical functions, and/or Dixon elliptical functions, a suitable k-space trajectory may also be determined based on for example Chebyshev polynomials, in particular generalized via Dickson polynomials, may be used. Furthermore, a k-space trajectory may be determined via Fourier sequences for one or more of the x-/y-/z-gradients, generating a mathematical optimization task and numerically solving the same. Accordingly, even though the present disclosure is described with reference to Jacobi theta functions as an exemplary embodiment, the disclosure is not limited thereto.

An advantage of this approach is that it allows for subsequent correction of an incorrectly set FOV without additional acquisition of MRI data. Hence, the amount of repeated scans can be reduced. Moreover, a scan may be started immediately after positioning the patient on the patient table. Hence, instead of spending time for carefully selecting a FOV after positioning the patient on the table followed by a subsequent MRI scan with data acquisition limited to the selected FOV, the time of the MRI scanner may be used more efficiently by directly starting with the proposed MRI data acquisition e.g. using the tailored k-space trajectory independent of an a-priori defined FOV and to reconstruct an MRI image aposteriori for any desired field of view.

In an earlier publication of the inventors (Speidel et al., "Efficient low-discrepancy k-space sampling using highly adaptable Seiffert Spirals", IEEE Transaction on Medical Imaging, vol. 38, no. 8, pp. 1833-1840, 2019) it was discussed that efficient low-discrepancy k-space sampling can be provided using highly adaptable Seiffert spirals. However, the earlier publication still followed the conventional path of using an a-priory defined field-of-view during acquisition of MRI data.

The k-space trajectory for acquisition of the k-space MRI data can be constructed based on (a) a low-discrepancy sampling of the frequency domain k-space, which can be determined based on a desired maximum image resolution, and (b) by determining a sampling of the frequency domain k-space that provides an incoherent energy distribution in image space in case of undersampling in the k-space. It will be appreciated that in view of these boundary conditions, a plurality of respective k-space trajectories can be obtained by numerical optimization. An exemplary solution can be obtained based on one or more theta functions, optionally in combination with trigonometric functions. Gradient waveforms can be determined as a derivative thereof. The gradient waveforms can be applied to the magnetic field gradient coils and thereby provide a desired trajectory in k-space.

In an embodiment, the gradient waveforms can be determined based on different combinations of the four Jacobi theta functions $\theta_1$, $\theta_2$, $\theta_3$, $\theta_4$ also referred to as $\vartheta_{0,0}$, $\vartheta_{0,1}$, $\vartheta_{1,0}$, $\vartheta_{1,1}$ respectively in the three gradient channels. In this case, the gradient waveforms may further be continuously differentiable. An advantage is that they may be less prone to irregularities (non-linearities) of the gradient system. Possible waveforms for all gradient channels ($G_x$, $G_y$, $G_z$) may for example be provided by the following functions:

$$G_x(s,m)=\vartheta_{0,0}(s,m)\cdot\cos(sm^2),$$

$$G_y(s,m)=\vartheta_{0,0}(s,m)\cdot\sin(sm^2), \text{ and}$$

$$G_z(s,m)=\vartheta_{0,1}(s,m),$$

wherein s is a parameter defining a length of the waveform and m may adapt the waveform to underlying hardware properties of the gradient system available in the MRI system.

In the following, some terms which are used throughout the application, shall be shortly explained and defined. As used herein, a magnetic field gradient can also be referred to as gradient coil. A field-of-view-independent 3D k-space trajectory can refer to a 3D k-space trajectory that is independent of an a-priori defined field-of-view. It shall be understood that the gradient waveform in MRI can be deduced from the k-space waveform by differentiation.

The FOV-independent 3D k-space trajectory may optionally be determined based on a desired image resolution. In addition or in the alternative, the FOV-independent 3D k-space trajectory may be determined based on a desired, possible or available image acquisition time. Image resolution information and/or acquisition time information may be obtained and the k-space trajectory may be adapted accordingly. Thereby, additional boundary conditions may be considered in determining a most appropriate 3D k-space trajectory. Both the image resolution and acquisition time may be known prior to acquisition of the MRI data. For example, for a given clinical question a limited resolution may be sufficient. Alternatively, for example in an emergency setting, the acquisition time should be limited for patient safety.

The field-of-view independent 3D k-space trajectory can be based on one or more Jacobi theta functions. The plurality of Jacobi theta functions can be adapted to provide low coherent aliasing properties below a predetermined threshold in the magnetic resonance image. A low-coherence theta function or theta function having low aliasing properties can be defined as a function having a ration of a peak of a point spread function of said function compared to a non-center local maximum being below a predetermined threshold. In addition or in the alternative, the k-space trajectory for acquisition of k-space MRI data can have a low discrepancy, i.e. a discrepancy value below a predetermined threshold. The k-space trajectory for acquisition of k-space MRI data can be adapted such that an undersampling artefact behavior in the image domain is white-noise like. The inventors have found that beneficial properties can be achieved given by an artefact behavior which is widely comparable to the introduction of white noise in the image domain. This may also allow efficient and effective post-processing with existing signal processing algorithms such as compressed sensing.

One or more of the Jacobi theta functions can be provided by at least one of $\theta_1$, $\theta_2$, $\theta_3$, $\theta_4$ wherein $$\theta_1(z,q) := \sum_{n=-\infty}^{\infty} (-1)^{n-1/2} q^{(n+1/2)^2} e^{(2n+1)iz}$$

$$\theta_2(z,q) := \sum_{n=-\infty}^{\infty} q^{(n+1/2)^2} e^{(2n+1)iz}$$

$$\theta_3(z,q) := \sum_{n=-\infty}^{\infty} q^{n^2} e^{2niz}$$

$$\theta_4(z,q) := \sum_{n=-\infty}^{\infty} (-1)^n q^{n^2} e^{2niz},$$

wherein $q\in \mathbb{C}$ and $|q|<1$, $n\in \mathbb{N}$. These functions have been found to enable MRI image acquisition without FOV selection since they can result in sufficiently random sampling of the k-space, such that any FOV might be reconstructed from the underlying dataset since only aliasing artefacts that have white noise like-character may be introduced.

A field-of-view independent 3D k-space trajectory can comprise a plurality of different interleaves in k-space based on different Jacobi theta functions. A plurality of Jacobi theta functions having low-coherent undersampling or aliasing properties may be used. Different interleaves can refer to different acquisition shots. The k-space may thus be sample using a plurality of interleaves so as to cover the k-space with a plurality of interleaves. A length of an interleave can be determined based on a predetermined readout time and or resolution. A maximum k-space value determines the resolution. A FOV may be indicated by a k-space density.

At least one of the Jacobi theta functions, in particular a superposition of theta functions, may be different from a Jacobi elliptic function, in particular different from a Seiffert spiral. This can allow advantageous reconstruction with low artifacts.

Generally speaking, the k-space MRI data may be achieved by sampling the k-space in a randomized manner, in particular based on one or more Jacobi theta functions. The inventors have found that as long as the k-space is sufficiently randomly sampled, any FOV may be reconstructed (afterwards) from the underlying MRI data set, since in image space the undersampling of such an acquisition may substantially translate to white-noise, i.e. provide a white-noise like behavior, which may be filtered out. In other words, the distribution of sampling points in k-space does advantageously not follow a regular or symmetric pattern. Based e.g. on Jacobi theta functions, a pseudo-random sampling or low discrepancy sampling in frequency domain k-space can be provided that leads to low coherent artefacts in image space.

Determining the k-space trajectory for acquisition of k-space MRI data may comprise retrieving one or more predetermined FOV independent trajectories from a storage or predetermined FOV independent trajectories. In other words, a library of predetermined FOV independent trajectories may be used. Because no patient-based FOV adaptation is required, it is possible to use pre-calculated trajectories. This can reduce acquisition time and may help to increase patient throughput or enable more detailed examination. Optionally, a FOV-independent trajectory may be retrieved from the storage of predetermined FOV independent trajectories based on a desired resolution and/or based on desired scan time.

It is to be understood that the features mentioned above and those yet to be explained below may be used not only in the combination respectively indicated, but also in other combinations or separately, without departing from the scope of the present invention.

BRIEF DESCRIPTION OF THE DRAWINGS

These and other aspects of the invention will be apparent from and elucidated with reference to the embodiment(s) described hereinafter. In the following drawings

DETAILED DESCRIPTION OF ASPECTS OF THE INVENTION

Figure 1:
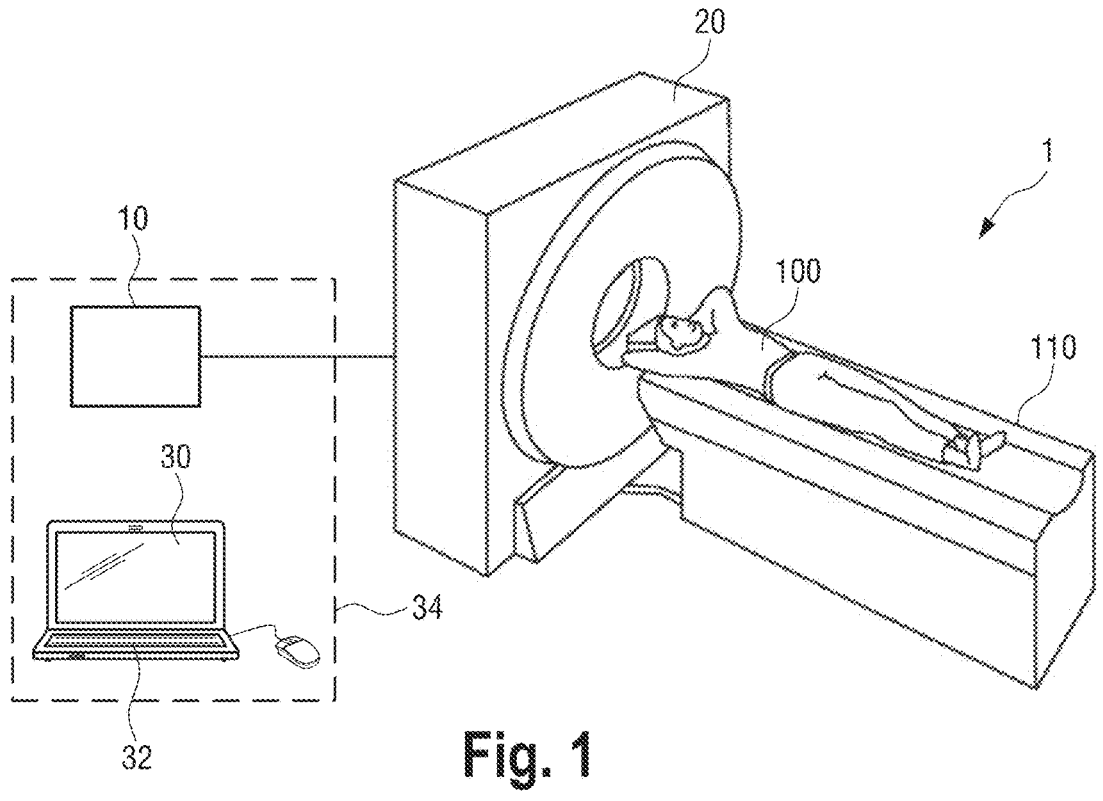
FIG. 1 shows a schematic diagram of an exemplary embodiment of an MRI system.

FIG. 1 schematically shows an exemplary embodiment of a magnetic resonance imaging (MRI) system for acquisition of a magnetic resonance image. The system is therein denoted in its entirety by reference numeral 1. The MRI system 1 comprises a device 10 for determining a trajectory for acquisition of an MRI image, an MRI scanner 20 and an image reconstruction device 30.

In accordance with an aspect of the present disclosure, the device 10 for determining the trajectory for acquisition of an MRI image can adapted to determine a k-space trajectory for acquisition of k-space MRI data independent of an a-priori defined field of view, FOV. In particular, said k-space trajectory may comprise a field-of-view independent 3D k-space trajectory based on one or more Jacobi theta functions. The MRI scanner 20 can be adapted to acquire the k-space MRI data, wherein a gradient waveform corresponding to said field-of-view independent k-space trajectory is applied to magnetic field gradients of the MRI scanner. The MRI scanner 20 can be a commercially available MRI scanner comprising a (superconducting) magnet as well as the usual gradient coils and radio frequency coils for excitation and signal acquisition. The image reconstruction device 30 can comprise an interface for selecting a desired field of view for the magnetic resonance image after acquiring the k-space MRI data. For example a conventional human-machine-interface 32 for computers may be provided. The image reconstruction device can be adapted to construct the magnetic resonance image based on the desired field of view from the acquired k-space MRI data previously provided by the MRI scanner 20. It shall be understood that one or more of these system elements may be co-integrated. For example, the device 10 and the reconstruction device 30 may be implemented in form of a control station or computer 34.

Figure 2:
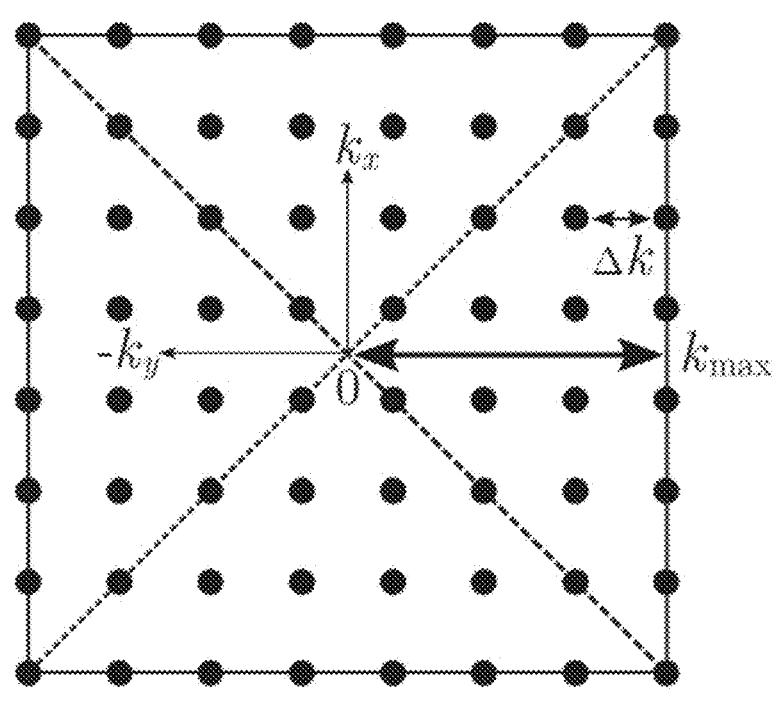
FIG. 2 shows a diagram of conventional k-space sampling on a regular grid-pattern.

FIG. 2 shows a diagram of conventional k-space sampling on a regular grid-pattern. K-space is a commonly used frequency domain representation for the acquisition of MRI data. The frequency domain data is then transformed into the image domain to provide an image for review by a radiologist. The separation Ok of neighboring measurement points in frequency domain defines the size of the MRI field of view. The maximum value $k_{max}$ in turn defines the maximum resolution in the image domain. Hence, for imaging a desired field of view with sufficient resolution to meet the Nyquist theorem a rather high density of sampling points in frequency domain has to be provided, which may lead to slow signal acquisition. Accordingly, conventional MRI systems always request an operator to select a limited field of view as a first step prior to acquisition of MRI data, even if more advanced acquisition schemes such as 3D cones sampling are used.

Undersampling in the spatial frequency domain can be used to shorten acquisition times in magnetic resonance imaging (MRI). Thereby, the violation of Nyquist's theorem leads to the emergence of aliasing artefacts. Such artefacts can be addressed with parallel or auto calibration methods such as Compressed Sensing (CS) (see M. Lustig et al., "The application of compressed sensing for rapid MR imaging," Magn 11 eason Med, vol. 58, no. 6, pp. 1182-1195, 2007, or S. Foucart and H. Rauhut, "A mathematical introduction to compressive sensing," Birkhäuser, Basel, 2013, vol. 1, no. 3, which are incorporated herein by reference). Especially for three-dimensional applications resulting long acquisition times often limit clinical applications.

With the present disclosure, a low-discrepant and efficient k-space coverage may be provided. A sampling scheme may be provided that leads to an advantageous sampling point spread function (PSF$_S$) for the (angular) undersampled case. The PSF$_S$ may be adapted to provide a low-coherent energy distribution in the PSF$_S$ for nearly arbitrary undersampling factors so as to introduce aliasing artefacts with a (noise-like) power spectrum whose characteristics are merely independent on the degree of undersampling.

The inventors found that using gradient waveforms derived from a field of view; FOV, independent k-space trajectory, in particular derived from Jacobi theta functions, may advantageously be used for acquisition of MRI image data. For example the use of Jacobi theta functions allows for a variety of highly adaptable k-space interleaves while maintaining low-coherent sampling properties. The inventors found, that low-coherent aliasing properties offer the possibility of reconstructing arbitrary FOVs by only introducing random noise-like aliasing artefacts. This leads to a situation in which a MRI trajectory can be constructed by totally neglecting the desired imaging FOV. Accordingly, and FOV-independent MRI trajectory is provided based on one or more Jacobi theta functions. A target resolution and/or a predefined scan time can be provided as an input. However, in contrast to conventional approaches for determining a 3D MRI trajectory, no FOV information is required. The trajectory is just adapted to meet a given resolution. A total number of interleaves may be derived from a desired total scan duration. As a further advantage, the presented concept can mark a well-suited precondition for the combination with a CS reconstruction, especially with the ability of achieving variable sampling densities around the center of k-space.

Figure 3:
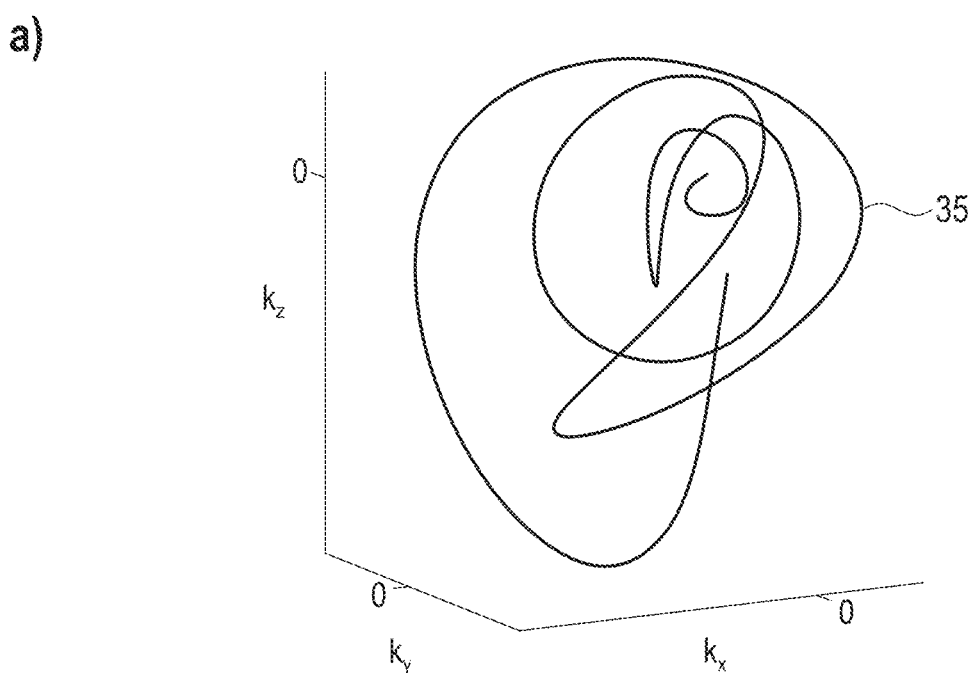
FIG. 3 shows an exemplary trajectory in k-space according to an aspect of the present invention.
Figure 3:
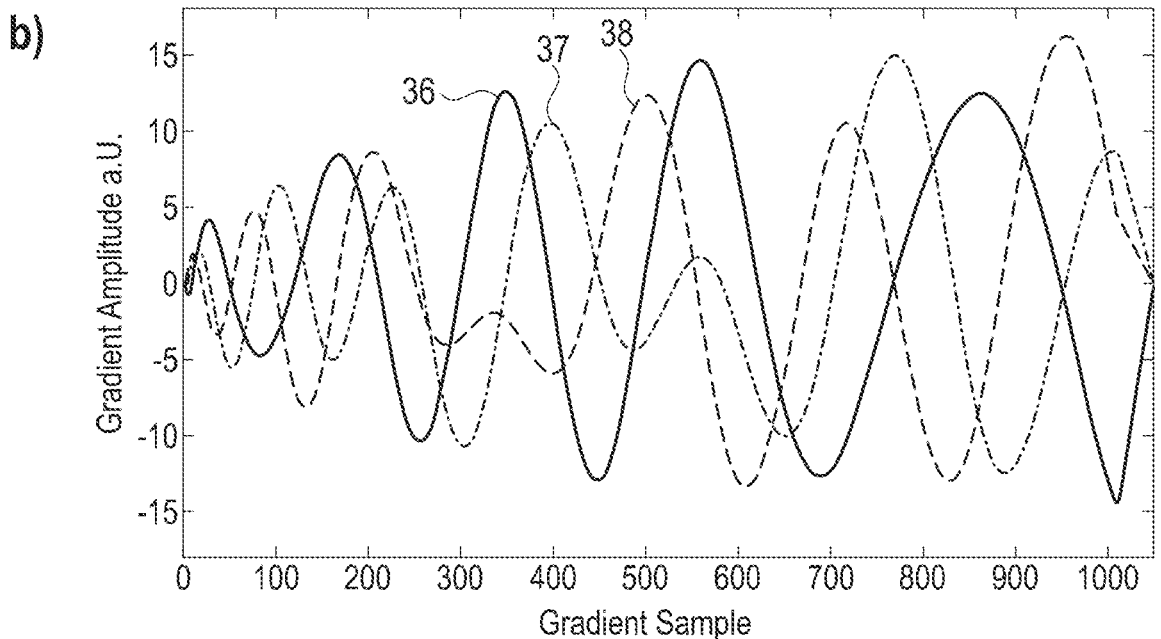

FIG. 3*b* show exemplary waveforms for the three gradient. The horizontal axis denotes the sequence of gradient samples. The vertical axis denotes the gradient amplitude in arbitrary units. The gradient amplitude may optionally be expressed in mT/m. Possible waveforms for all gradient channels ($G_x$, $G_y$, $G_z$) may for example be provided by the following functions:

$$G_x(s,m) = \vartheta_{0,0}(s,m) \cdot \cos(sm^2),$$

$$G_y(s,m) = \vartheta_{0,0}(s,m) \cdot \sin(sm^2), \text{ and}$$

$$G_z(s,m) = \vartheta_{0,1}(s,m),$$

wherein s is a parameter defining a length of the waveform and m may adapt the waveform to underlying hardware properties of the gradient system available in the MRI system. In FIG. 3*b*, channel $G_x$ is denoted by reference numeral 36, $G_y$ denoted by reference numeral 37 and $G_z$ denoted by reference numeral 38. The resulting sampling in frequency domain or k-space is illustrated in FIG. 3*a*.

With the proposed signal acquisition, the proposed method may allow to use image information that may lie outside of the actual image region to be displayed. Moreover, the signal acquisition of 3D MRI may be accelerated.

Figure 4:
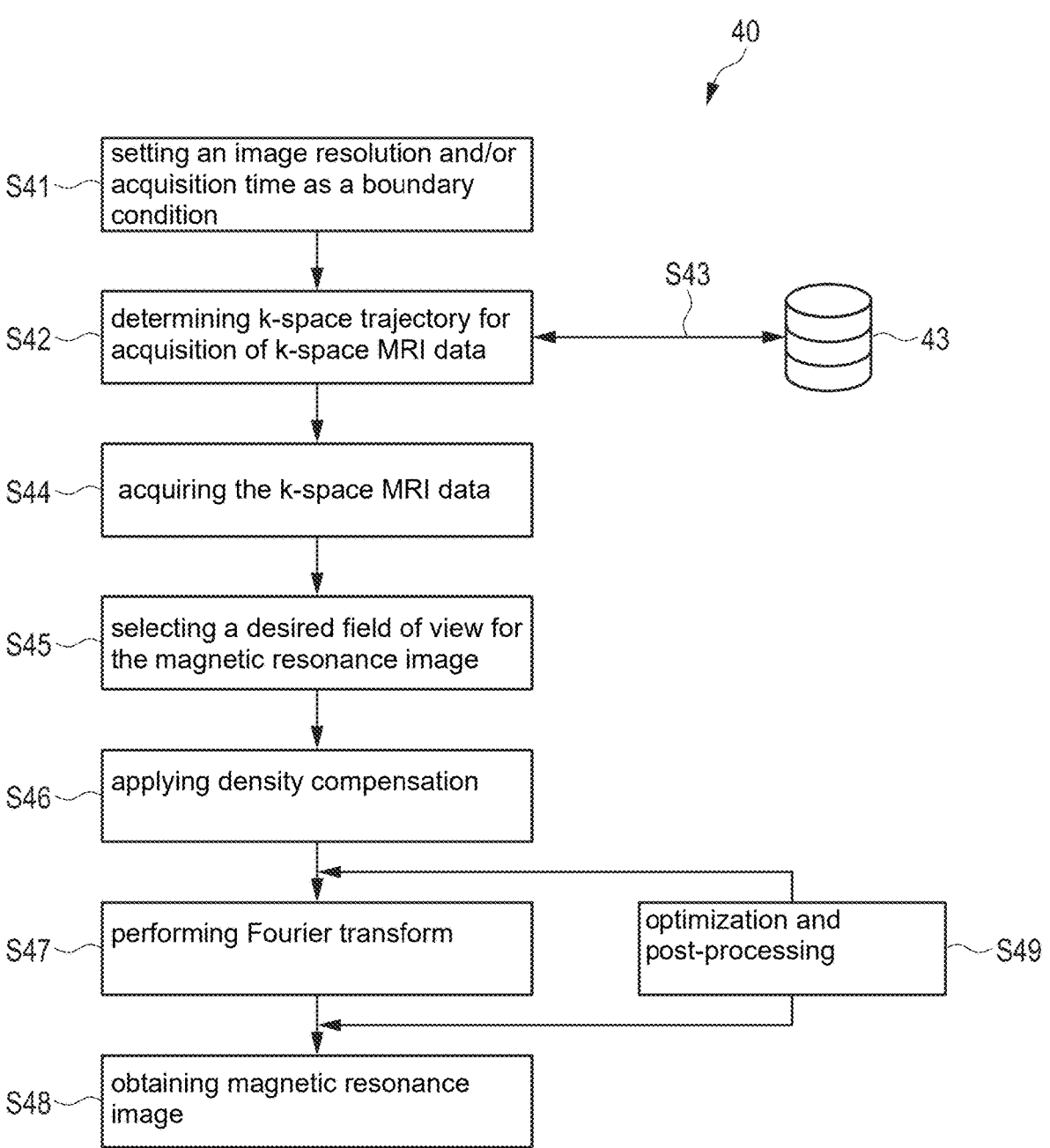
FIG. 4 shows a flow chart of an exemplary method.

FIG. 4 shows a flow chart of an exemplary method 40 for acquisition of a magnetic resonance image independent of an a-priori defined field-of-view, FOV. In an optional initial step S41, an image resolution and/or acquisition time may be set as a boundary condition. In step S42, a k-space trajectory for acquisition of k-space MRI data in the frequency domain is determined. The k-space trajectory comprises a FOV-independent 3D k-space trajectory. A plurality of different trajectories may be determined for acquisition of several interleaves. Optionally, the one or more trajectories can be obtained from a storage 43 of predetermined FOV independent trajectories in step S43. The trajectories may be obtained based on the aforementioned boundary conditions.

In step S44, the k-space MRI data is acquired using the MRI scanner. A gradient waveform corresponding to the determined field-of-view independent k-space trajectory is applied to magnetic field gradients of the MRI scanner. In step S45, i.e. after having acquired the k-space MRI data in step S44, a desired field of view for the magnetic resonance image is selected. The magnetic resonance image is constructed based on the desired field of view from the acquired k-space MRI data.

In a more elaborate optional embodiment, in step S45 the data can be interpolated to a reconstruction geometry with selection of the size of the FOV. In an optional step S46 a density compensation may be applied before performing a Fourier transform in step S 47 to obtain the magnetic resonance image in step S48. Optional further optimization and post-processing such as compressed sensing may be performed in step S49 before or after the Fourier transform in step S47. Optionally, the post-processing in step S49 may be controlled based on a result of S47, for example by in terms of a preparation in step S47 for the post-processing in step S49.

In the following, some underlying theoretical considerations will be explained to facilitate the understanding of aspects of the invention.

II.A UNDERSAMPLING AND NYQUIST'S THEOREM

In the case of Cartesian k-space sampling, Nyquist's theorem states that the distance $\Delta k_i$ between adjacent sampling points has to fulfil the condition $\Delta k_i \leq 1/FOV_i$, where FOV is the field of view and i=x, y, z reflects the standard three-dimensional Euclidean basis. A violation of the given sampling condition leads to aliasing i.e. interference of image information that is not represented in the acquired spatial frequency data. Cartesian undersampling leads to aliasing artefacts in the spatial domain known as "ghosts", while in the case of radial (polar) undersampling streak artefacts appear.

The reciprocal proportionality between FOV and sampling density concludes that the maximum FOV (along each axis) which can be reconstructed using the acquired data is given by $FOV_i = 1/\Delta k_i$. Therefore, aliasing artefacts appear in every reconstructed FOV that violates the initial Nyquist condition, while aliasing properties are governed by the corresponding (sampling) point spread function of the k-space sampling scheme. The $PSF_S$ indicates how the information associated with a point source in the original image is spread out in the reconstructed image. A Delta peak is therefore an ideal PSF since only the information of one point in the original image corresponds to one point in the reconstructed image. However, due to the limitation of discrete and finite sampling, the Delta peak is spread out which leads to a decrease in resolution in the reconstructed image. But consequently, the full width at half maximum of the center peak of the $PSF_S$ can be seen as an appropriate measure for image sharpness also in a relative way by allowing comparisons of different $PSF_S$, while the side-lobe behavior indicates coherent aliasing properties.

In a direct reconstruction, the reconstructed image $\phi$: $\psi_\phi$ can be obtained by a convolution of the original image $\psi$ with the associated $PSF_S$ $\phi$: $\psi_\phi = \psi * \phi$. In the case of a compactly supported image $\psi \in L^2(\mathbb{R}^3)$ i.e. $\psi$ may have a square Lebesque integrable representation, $\phi$ can be expressed as $$\phi(X) = \tag{1}$$
$$\sum_p \exp\{2\pi i(x k_x(p) + y k_y(p) + z k_z(p))\} \cdot \rho(k_x(p), k_y(p), k_z(p)),$$

with X=(x, y, z) and the sum can be taken over all sampled points in k-space with coordinates ($k_x$, $k_y$, $k_z$. Additionally, $\rho$ can allow for the introduction of a density compensation function when sampling on a non-equidistant grid. Such a density compensation may only influence the peak/side-lobe amplitudes in the $PSF_S$ but not their overall position. This can be simplified by assuming a symmetrically sampled k-space about the origin, leading to a vanishing imaginary part of the $PSF_S$. Under this assumption $$\phi(X) = \tag{2}$$
$$\sum_p \cos\{2\pi i(x k_x(p) + y k_y(p) + z k_z(p))\} \cdot \rho(k_x(p), k_y(p), k_z(p)).$$

Therefore, all $PSF_S$ may be constructed by a sum of cosine terms, constructively and destructively interfering in image space. Considering two adjacent points $p_1$ and $p_2$ in k-space may lead to an interference that can be determined by the expression $$T(X) = \cos\{2\pi(x k_x(p_1) + y k_y(p_1) + z k_z(p_1))\} + \cos\{2\pi(x k_x(p_2) + y k_y(p_2) + z k_z(p_2))\}. \tag{3}$$

Choosing e.g. the two points $k_1=(\varepsilon, 0,0)$ and $k_2=(0, \varepsilon, 0)$ may result in $$T(X)=\cos\{2\pi\varepsilon x\}+\cos\{2\pi\varepsilon y\}. \quad (4)$$

For $\varepsilon=1$, the two cosine terms may show a maximum constructive interference with repeating peaks being separated by $\varepsilon$ in x- and y-direction. Due to the convolution, the repetitive pattern of interference may only cause aliasing artefacts if the extension of the image is larger than $1/\varepsilon$ along the x- or y-direction. This finding corresponds to the previously mentioned Nyquist condition (FOV=$1/\Delta k$.

Considering the situation in which a spherical k-space of radius $k_{max}$ is Nyquist sampled within a sphere of e.g. radius $0.5\ k_{max}$ and undersampled elsewhere, then the undersampled region will generate aliasing artefacts within a FOV that is calculated with respect to the sampling density within the Nyquist sampled volume. The nature of random sampling may lead to various spacings between neighboring k-space points and therefore to the interference of a multitude of cosine waves in image space. The resulting pattern of interference in image space consists of numerous regions of constructive and destructive interference, spreading the aliased energies more and more homogeneous over the imaging space, as the variations in point spacings and their spatial orientations vary.

Additionally, as long as a certain random character in the k-space sampling scheme is preserved, the full width at half maximum (FWHM) of the $PSF_S$ has been found to remain widely unchanged as the undersampling factor increases, leading to a conservation of image sharpness. The inventors found that as long as k-space is sufficiently random sampled, any FOV might be reconstructed from the underlying dataset by only introducing aliasing artefacts that have a white noise-like character. The white noise-like character may in turn be addressed with image post-processing.

II.B THETA FUNCTIONS

The inventors recognized that in physics, Jacobi elliptic functions can be used to describe the motion of a frictionless pendulum, where the real part of the period determines the time of the pendulum to go through one full cycle. Additionally, the imaginary period describes the same periodicity but under the transformation t→it, i.e. the sign of all forces is reversed. The Jacobi elliptic functions e.g. sn(it,l) must therefore be periodic as a function of time t and spatial variable l, making them double periodic functions.

Each Jacobi elliptic function can be fundamentally represented by a fraction of Jacobi theta functions e.g.:

$$sn(u,l) = \frac{\theta_3\theta_1(z=0,q)}{\theta_2\theta_4(z=0,q)} \text{ with } l = \left(\frac{\theta_2(z=(0,q)}{\theta_3(z=(0,q)}\right)^2 \quad (5)$$

and $$u = \pi\theta_3^2 z.$$

The four theta functions $\theta_i$ with i=1, 2, 3, 4 can be defined $\forall q\in\mathbb{C}$ with $|q|<1$ as follows:

$$\theta_1(z,q) := \sum_{n=-\infty}^{\infty} (-1)^{n-1/2} q^{(n+1/2)^2} e^{(2n+1)iz} \quad (6)$$

-continued $$\theta_2(z,q) := \sum_{n=-\infty}^{\infty} q^{(n+1/2)^2} e^{(2n+1)iz} \quad (7)$$

$$\theta_3(z,q) := \sum_{n=-\infty}^{\infty} q^{n^2} e^{2niz} \quad (8)$$

$$\theta_4(z,q) := \sum_{n=-\infty}^{\infty} (-1)^n q^{n^2} e^{2niz}. \quad (9)$$

For efficient numerical implementation, these traditional representations using infinite sums, may optionally be transformed and adapted for an efficient numerical implementation. Furthermore, all theta functions are analytic functions for z, $q\in\mathbb{C}$ and $|q|<1$. In terms of MRI, the gradient waveform can be deduced from the k-space waveform by differentiation. Assuming a k-space interleave based on theta functions leads to a steady and continuously differentiable gradient waveform which makes the latter less prone to system imperfections. For completeness, a list of derivatives of all theta functions is given in the following $\forall z, q\in\mathbb{C}$ and $|q|<1$:

$$\theta_1'(z,q) = 2\sqrt[4]{q} \sum_{n=0}^{n=\infty} (-1)^n q^{n(n+1)}(2n+1)\cos((2n+1)z) \quad (10)$$

$$\theta_2'(z,q) = -2\sqrt[4]{q} \sum_{n=0}^{\infty} q^{n(n+1)}(2n+1)\sin((2n+1)z \quad (11)$$

$$\theta_3'(z,q) = -4\sum_{n=1}^{\infty} q^{n^2} n\sin(2nz) \quad (12)$$

$$\theta_4'(z,q) = -4\sum_{n=1}^{\infty} (-1)^n nq^{n^2} \sin(2nz). \quad (13)$$

II.C GENERALIZED FOV

For many conventional multi-shot k-space trajectories e.g. radial sampling, the condition $\Delta k_i \leq 1/FOV_i$ with i=x, y, z is not necessarily verified with respect to a Cartesian sampling grid. It appears more convenient to evaluate an upper limit by using Pythagoras' theorem in 2D or 3D k-space, i.e.

$$\Delta k_{max} = \max_{\{d\in K\}}\left(\sqrt{\Delta k_{x,d}^2 + \Delta k_{y,d}^2 + \Delta k_{z,d}^2}\right),$$

where d is the set of all distances in k-space K between points that are nearest neighbors and do not belong to the same k-space interleave or read-out. Since $\Delta k_{max}\geq\Delta k_i$, $d\forall d\in K$ and i=x, y, z, Nyquist's theorem is indeed fulfilled if $(1/FOV_i)\geq\Delta k_{max}$. While e.g. in the case of radial sampling, this evaluation can be restricted to the sampling point of each read-out that is farthest away from the center of k-space, it may require further elaboration for the case of any quasi-random sampling point distribution.

Figure 5:
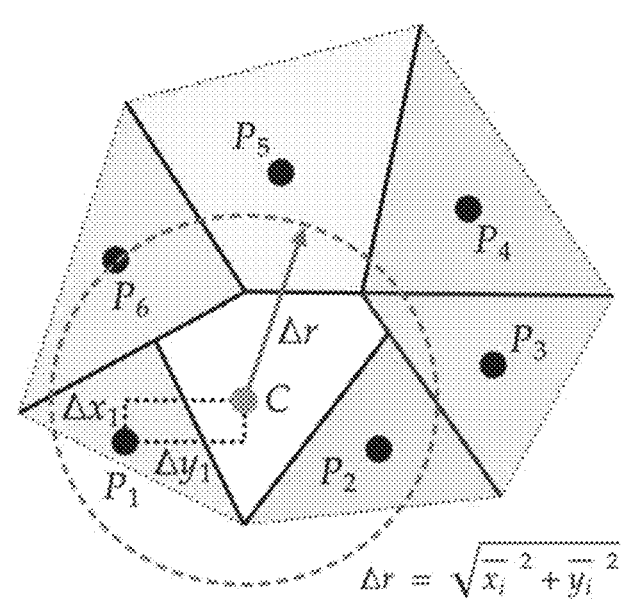
FIG. 5 shows a schematic representation of several Voronoi cells in two-dimensional k-space.

In the scope of this disclosure it may be useful to optionally extend the estimation of a $\Delta k_{max}$ even further since the later introduced distribution of sampling points will not follow any regular or symmetric pattern. FIG. 5 shows one point of interest C in k-space with six surrounding nearest neighbors $P_i$ with i=1, . . . , 6, for simplification in two dimensions. FIG. 5 shows a schematic representation of seven Voronoi cells in a two-dimensional k-space. In the given example, six nearest neighbors of the point of interest C are used for the definition of the generalized FOV.

The direct distances $d_{C,P_i}$ between C and each $P_i$ are calculated and the mean value of all six distances defines a radius $\Delta r$ around C. This radius can then define a generalized FOV for C by setting $FOV_C = 1/\Delta r_C$ but also for every other point in k-space following an equal calculation. In the three dimensional case, $\Delta r$ defines the radius of a sphere, from which an equal FOV along each direction is derived. The selection of six nearest neighbors can ensure (for the later described trajectory) that $\Delta r$ is derived from the expression $$\Delta r = \sqrt{\overline{\Delta x_i}^2 + \overline{\Delta y_i}^2 + \overline{\Delta z_i}^2}$$

with $\Delta x_i \neq 0$, $\Delta y_i \neq 0$, and $\Delta z_i \neq 0$, i.e. the radius can define a spherical (3D) volume. The given definition allows the assignment of an isotropic FOV (lower bound) to various specific regions and points in k-space.

In the following, some methodological considerations will be explained to facilitate the understanding of aspects of the invention.

III.A INTERLEAVES IN K-SPACE BASED ON THETA FUNCTIONS

The inventors recognized that making use of Jacobi theta functions may give rise to the possibility of constructing a multitude of inherently different k-space waveforms. It was found that a k-space trajectory for acquisition of k-space MRI data can be determined in particular based on one or more Jacobi theta functions such that a FOV-independent 3D k-space trajectory can be realized.

FIG. 6a shows two different exemplary k-space waveforms of arbitrary length, for which the $k_x$ and $k_y$ components are once based on $\theta_1$ (see curve 61) and once on $\theta_4$ (see curve 62). A projection of both waveforms into the $k_x$-$k_y$-plane is shown in FIG. 6b. Both interleaves are shown in three-dimensional k-space in FIG. 6a and as a plane projection in FIG. 6b.

Figure 6:
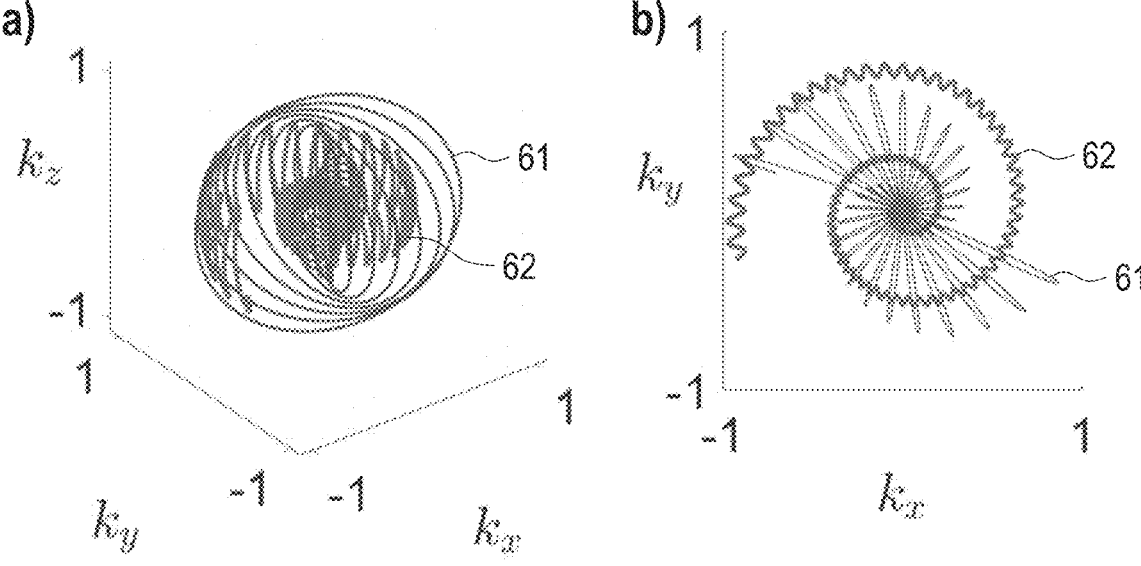
FIG. 6 shows diagrams of two exemplary interleaves each based on different Jacobi theta functions.

The following exemplary waveform is meant to prove the imaging concept for a lower limit of read-out durations. The general waveform can be generated on the surface of a unit sphere according to the definition:

$$\zeta : \mathbb{R}_0^+ \to \mathbb{R}^3, s \mapsto \vec{\zeta}(s)$$

with $m \in (0,1)$ and $$\zeta_x(s,m) = \theta_1(s,m^2) \cdot \cos(s \cdot m^2) \tag{14}$$

$$\zeta_y(s,m) = \theta_1(s,m^2) \cdot \sin(s \cdot m^2) \tag{15}$$

$$\zeta_z(s,m) = \theta_2(s,m^2) \tag{16}$$

while m is a parameter to adapt the waveform to hardware limitations such as maximum gradient amplitudes and available slew-rates. The combination with sine and cosine terms in the first two components may allow for a modifiable change in direction per unit length while the symmetry along the z-direction may remain unchanged (FIG. 6). The length of the waveform can be determined by s and therefore the restriction $s \in [0,$ $s_{max}$] may be applied with $s_{max}$ being sufficiently large according to the desired resolution (corresponding to extension of k-space).

In order to construct a center-out k-space interleave, the distance of each point on the spiral w.r.t. the k-space center may be linearly scaled from 0 to $k_{max}$. The linearly increasing radius of the spiral points may then be element-wise multiplied with a function of the type $f(x) = x^\alpha$, where $\alpha \in \mathbb{R}^+$ may account for an additional density modulation (radial increment). At the same time, the length of the spiral may be calculated to correspond to a certain read-out duration and resolution.

As an example, a k-space interleave was constructed with m=0.5, based on a target resolution of 0.85 mm (isotropic). An extended oversampling of k-space center for a possible combination with Compressed Sensing can be achieved by setting $\alpha = 1.3$. In the given example, the complete trajectory consisted of 20,000 rotated interleaves with a maximum gradient strength of 21 mT/m and a slew-rate of 120 T/m/s. Thereby, the total number of read-outs was arbitrarily defined and was not based on any prior FOV estimation. The trajectory can optionally be optimized by minimizing its discrepancy. The resulting read-out duration for each interleave was 3.52 ms, in order to reach the boundary of the k-space sphere for the defined maximum gradient amplitude and slew-rate limits. Ten interleaves of the final trajectory are depicted in FIG. 7 for illustrative purposes.

Figure 7:
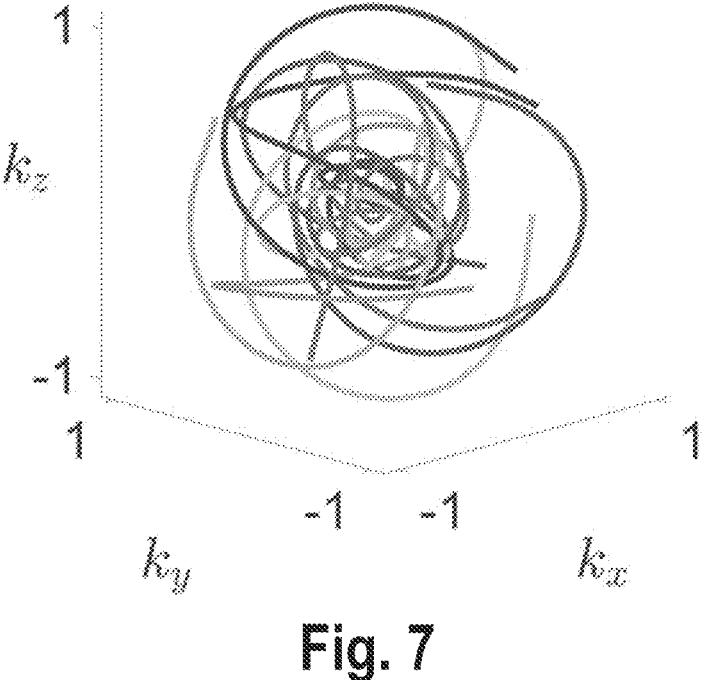
FIG. 7 shows a diagram of ten interleaves.

FIG. 7 illustrates a set of ten interleaves of the exemplary 3D $\zeta$-based spiral trajectory. The increased sampling density around the center of k-space can be clearly appreciated.

III.B PHANTOM IMAGING AND RECONSTRUCTION

In order to evaluate the aliasing behavior as well as imaging performance, an image quality phantom was measured for illustrative purposes. All phantom images were acquired using a 1.5 T wholebody MRI system (Achieva 1.5 T, Philips, Best, The Netherlands) and a 16-element SENSE Torso/Cardiac posterior coil (Philips, Best, The Netherlands) with 14 coil elements used for data acquisition. Image reconstruction for all 3D (based spirals was achieved in the following manner: after data acquisition, raw data were exported and processed with MATLAB (MathWorks, Natick, Massachusetts, USA). Images were obtained using gridding in combination with a 3D Voronoi tessellation. Gradient system delays were estimated and used to correct the trajectory before gridding. Further eddy current effects were compensated using a mono-exponential model with a time constant of $\tau = 39$ μs. No optional post-processing was applied to any presented image. Undersampling was created by calculating separate and optimized trajectories according to the presented method and parameters with 2,500, 1,665 and 1,250 interleaves, leading to undersampling factors R=8, 12 and 16 with respect to the fully sampled trajectory with 20,000 interleaves (R=1). All relevant scan parameters are listed in the following table of scan parameters for all four exemplary $\zeta$-based 3D spiral acquisitions:

|  | 3D $\zeta$-based Spiral |
| --- | --- |
| FOV/mm | 220 iso |
| Matrix | 258 iso |
| Res./mm | 0.853 iso |
| $T_R$/ms | 7.8 |
| $T_E$/ms | 0.343 |

-continued

|  | 3D $\zeta$-based Spiral |
| --- | --- |
| $T_{acq}$/ms | 3.52 |
| No. of Read-Outs | 20,000, 2,500, 1,665, 1,250 |
| Excitation | Block Pulse |
| Flip Angle/° | 20 |
| Sampl. BW/kHz | 425 |
| Max. Grd./mT/m | 21 |
| Max. Slew/T/m/s | 120 |
| Scan Duration/s | 156, 20, 13, 10 |

III.C SAMPLING POINT SPREAD FUNCTION

Based on the trajectories which were used for phantom imaging, four sampling point spread functions were calculated according to the undersampling factors R=1, 8, 12, 16. All $PSF_S$s were obtained independently by calculation of a Voronoi tessellation for every trajectory. Based on all normalized $PSF_S$s, the center-peak FWHM was determined in order to evaluate relative image sharpness with increasing undersampling factors.

III.D UNDERSAMPLING BEHAVIOR AND NOISE ANALYSIS

To provide an experimental estimate of the aliasing behavior, the noise characteristics of images acquired with the presented approach are compared to those of images acquired with 3D radial Kooshball sampling. For the 3D $\zeta$-based Spiral, two acquisitions with 20,000 and 1,250 excitations (R=16) were used. Additionally, a reference dataset was acquired with the vendor's 3D radial Kooshball trajectory, employing the same spatial resolution and choosing a FOV encompassing the whole phantom. Image reconstruction for the Kooshball trajectory followed the description given in the previous section for the 3D $\zeta$-based Spiral trajectory, except for the weighting calculation. Kooshball weights were calculated analytically, based on the symmetry of the sampling scheme. The radial dataset was retrospectively undersampled by a random selection of 1/R spokes.

Figure 12:
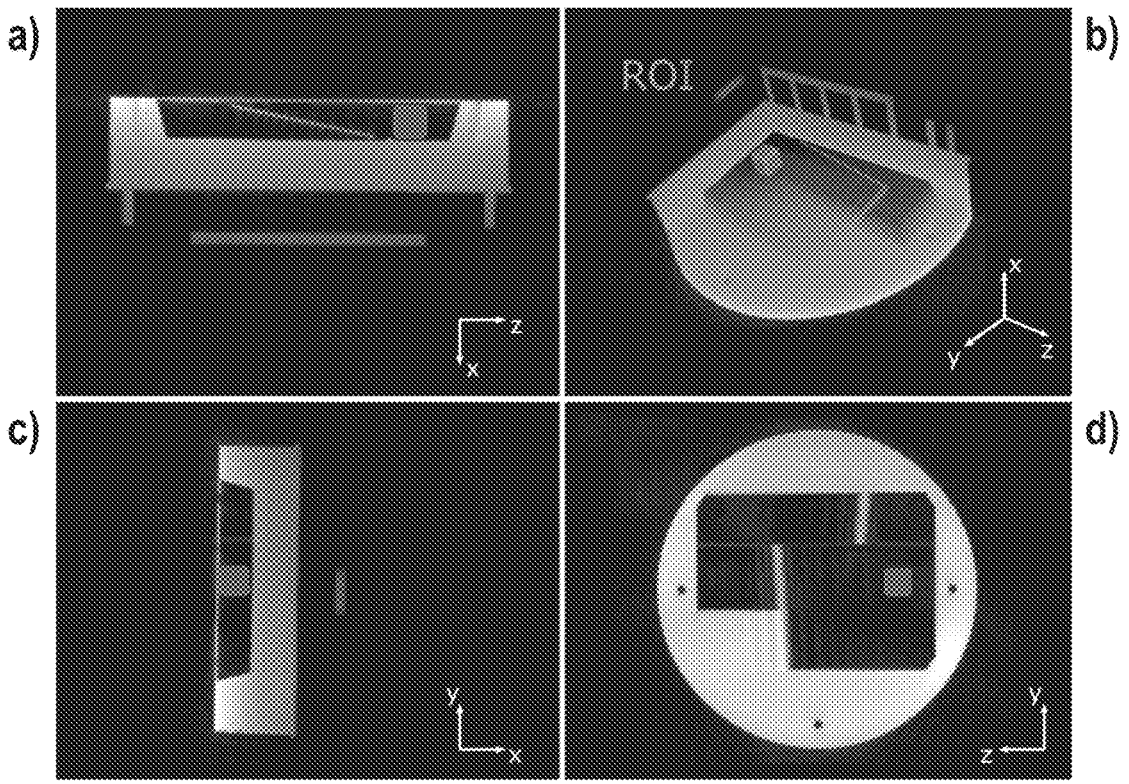
FIG. 12 shows a 3D sketch and different projections of the phantom for noise analysis.

In the given example, the region of interest (ROI) may correspond to an image region of ideally zero MR signal and may lie within an area of the phantom containing no fluid (see FIG. 12). Accordingly, the pixel intensities may be exclusively governed by artefacts and noise whose characteristics can be analyzed by consideration of the associated power spectrum. To facilitate the analysis of their characteristics (line shapes), all power spectra were normalized and are presented in arbitrary units. For each acquisition, the power spectra were averaged over all coil elements and evaluated with respect to the three geometrical axis to capture possible coherences.

Furthermore, the noise behavior is illustrated in the image domain by plotting the normalized values of $1-\log(I)$ for all defined undersampling factors, where I is the normalized image for which all coil elements were combined using sum of squares. In doing so, a slice (coronal orientation) of the 3D image was selected due to well-represented symmetric structures that contain no phantom liquid.

In the following, some experimental results will be explained to facilitate the understanding of aspects of the invention.

IV.A TRAJECTORY PROPERTIES

Referring again to the above example in terms of the generalized FOV, the presented exemplary trajectory with 20,0000 interleaves has the following properties: The Nyquist condition $$\Delta r_C \le \frac{1}{FOV_p} = (1/220)$$

mm is fulfilled within a sphere of radius $r_N=0.18\ k_{max}$, where $FOV_p$ is the (coronal) extension of the reconstructed FOV which contains the entire phantom. The smallest FOV that is stored within a sphere of radius $r_N=0.01 \cdot k_{max}$ in the given non-limiting example corresponds to 42-times the phantom dimension (200 mm). According to the definition, the Nyquist condition is not fulfilled for all points outside a sphere or radius $r_N$ but it is (in this region) fulfilled for some randomly distributed points. Nyquist's condition is always fulfilled along each interleave and is therefore excluded from the definition of the generalized FOV in the given example.

Since, in the given example, the number of played-out interleaves was arbitrarily defined and an enhanced center-oversampling was applied, the initial trajectory (20,000 interleaves) corresponds to an undersampling factor of $R_1 \approx 3.29$. This value was determined by calculating the mean generalized FOV for 10.000 arbitrarily selected points (computational complexity) of the specific trajectory and specifies that Nyquist's theorem is violated 3.29-times according to the definitions. Accordingly, the equally generated trajectory with 2,500 interleaves led to $R_2 \approx 6.43$, to $R_3 \approx 9.33$ for 1,665 interleaves and to $R_4 \approx 12.98$ for 1,250 interleaves. The intention of these numbers is merely to classify the presented trajectories than to enforce comparisons to other sampling schemes due to drastic differences in the distribution of points in k-space. For simplification, all images and results that correspond to undersampling factors $R_1, \ldots, R_4$ of the 3D $\zeta$-based spirals are denoted by $M_3$, $M_6$, $M_9$, $M_{13}$ according to the mean undersampling factors.

Figure 8:
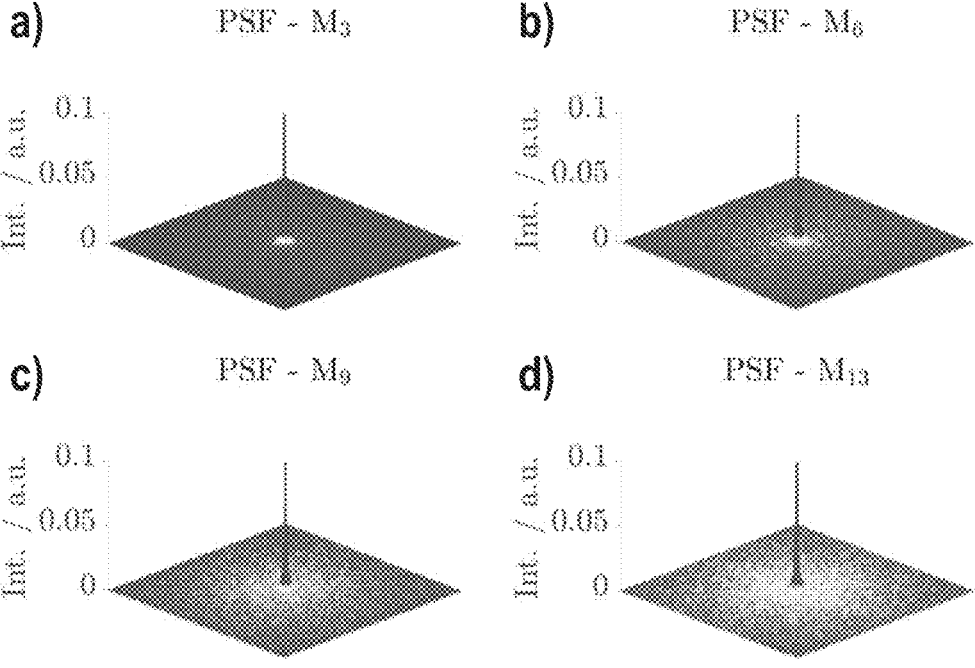
FIG. 8 shows diagrams of simulated point spread functions for different undersampling values.

FIG. 8 shows all associated sampling point spread functions for the four cases of undersampling in the xy-plane with z=0. The $PSF_S$ in a) corresponds to 3.29-fold undersampling, the $PSF_S$ in b) to 6.43-fold undersampling, c) and d) to 9.33-fold and 12.98-fold undersampling respectively.

By comparing successive undersampling factors, energies in the $PSF_S$s may emerge that do not seem to follow any ordered or symmetric pattern. Consequently, all $PSF_S$s appear to be governed by a low-coherent distribution of energies with an expected aliasing behavior that is (in its appearance) vastly similar to an introduction of white noise.

Figure 9:
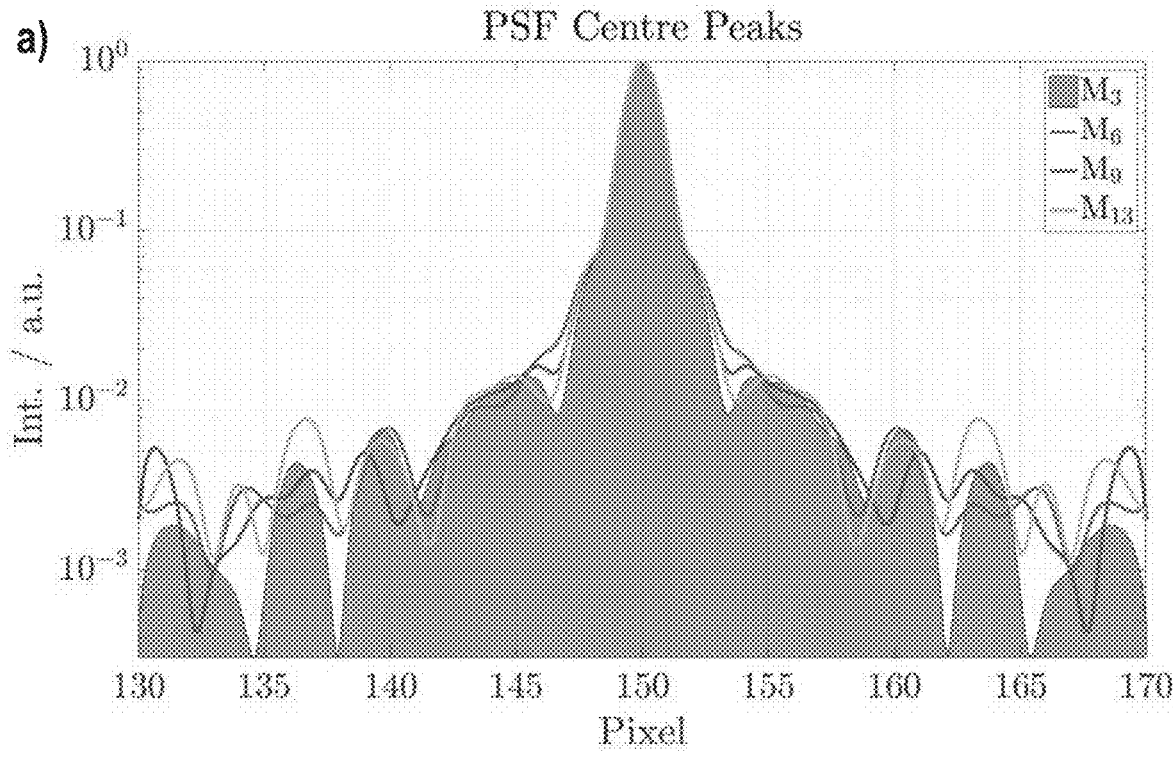
FIG. 9 shows logarithmic plots of the center regions of the point spread functions of FIG. 8.
Figure 9:
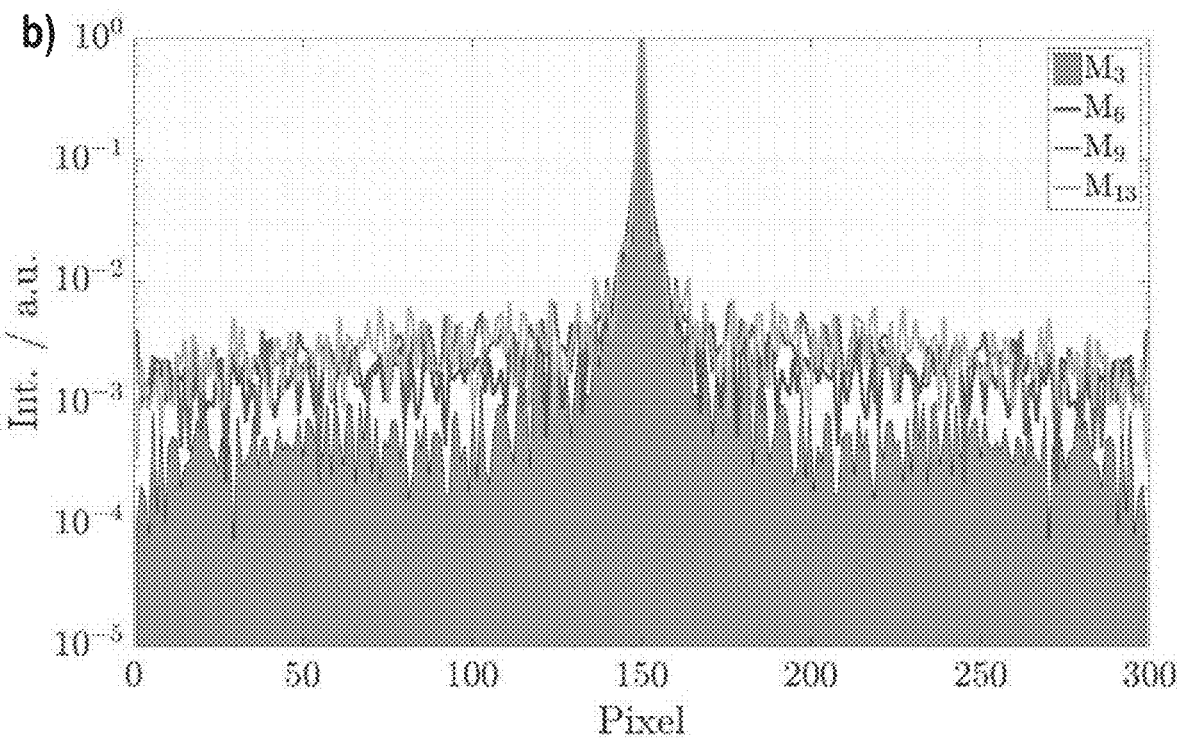

FIG. 9 shows a logarithmic plot of the center region of the four $PSF_S$s shown in FIG. 8a and a cross section of the entire $PSF_S$ in FIG. 8b. As the undersampling factor increases, an overall increase in energy can be appreciated in which the side-lobe behavior shows rarely signs of emerging coherences.

Furthermore, image sharpness is preserved for all undersampling factors by considering the FWHM of the $PSF_S$ center-peak which is $\approx 2.544$ pixel in width (mean) with a maximum deviation of 0.59% between the broadest peak ($M_{13}$: 2.549 px) and the narrowest peak ($M_9$: 2.534 px) of all undersampling $PSF_S$s. All values were obtained in non-logarithmic representation. This finding of retained sharpness is furthermore supported by the phantom images, presented in the following section.

IV.B UNDERSAMPLING BEHAVIOR AND NOISE ANALYSIS

Figure 10:
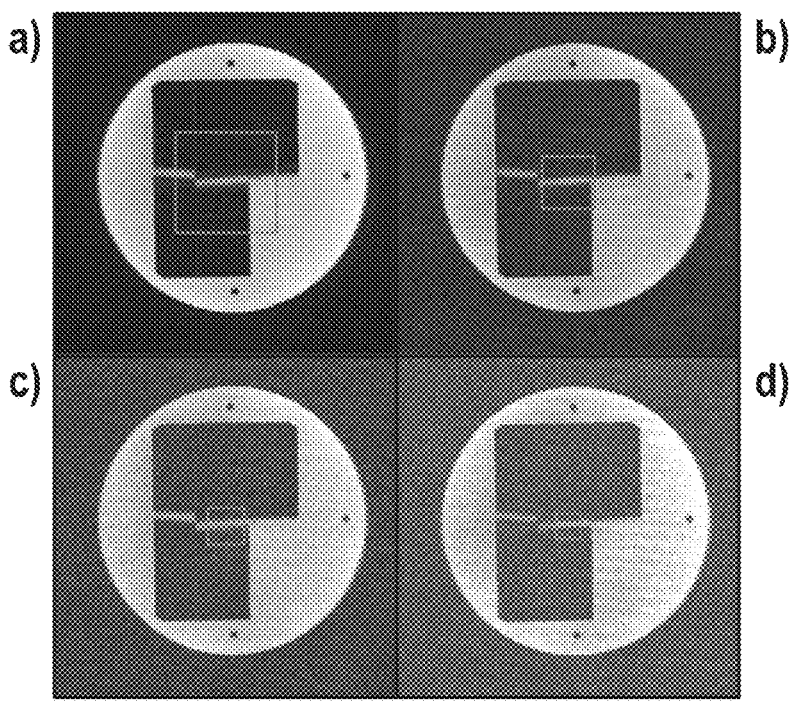
FIG. 10 shows a slice of an image quality phantom in coronal orientation acquired with various undersampling factors.

FIG. 10 shows a slice (coronal orientation) of the image quality phantom, acquired with the presented 3D $\zeta$-based spiral trajectories for each undersampling factor. All data was directly gridded and no additional image or data processing was applied before and after gridding. Furthermore, no sensitivity maps were used, in order not to alter the emerging imaging artefacts. FIG. 10 thus shows a slice of an image quality phantom (coronal orientation), acquired for various undersampling factors $R_1$ in a), $R_2$ in b), $R_3$ in c) and $R_4$ in d).

Each image in FIG. 10 contains a square marking that corresponds to the generalized FOV of the underlying (undersampled) trajectory of the 3D $\zeta$-based spiral acquisitions. The generalized FOV of $M_3$ is $\approx 67$ mm (isotropic), $\approx 34$ mm for $M_6$, $\approx 24$ mm for $M_9$ and $\approx 17$ mm for $M_{13}$. The reconstruction of a larger FOV, in this case of 220 mm (isotropic) for all datasets results in additional low-coherent aliasing artefacts which can clearly be appreciated. Despite uncorrected coil sensitivity profiles, all images appear non-degraded by coherent aliasing artefacts, especially visible in regions with no phantom fluid. As expected from the $PSF_S$ analysis, image sharpness is preserved and based on the optical impression equal for all investigated undersampling factors.

Figure 11:
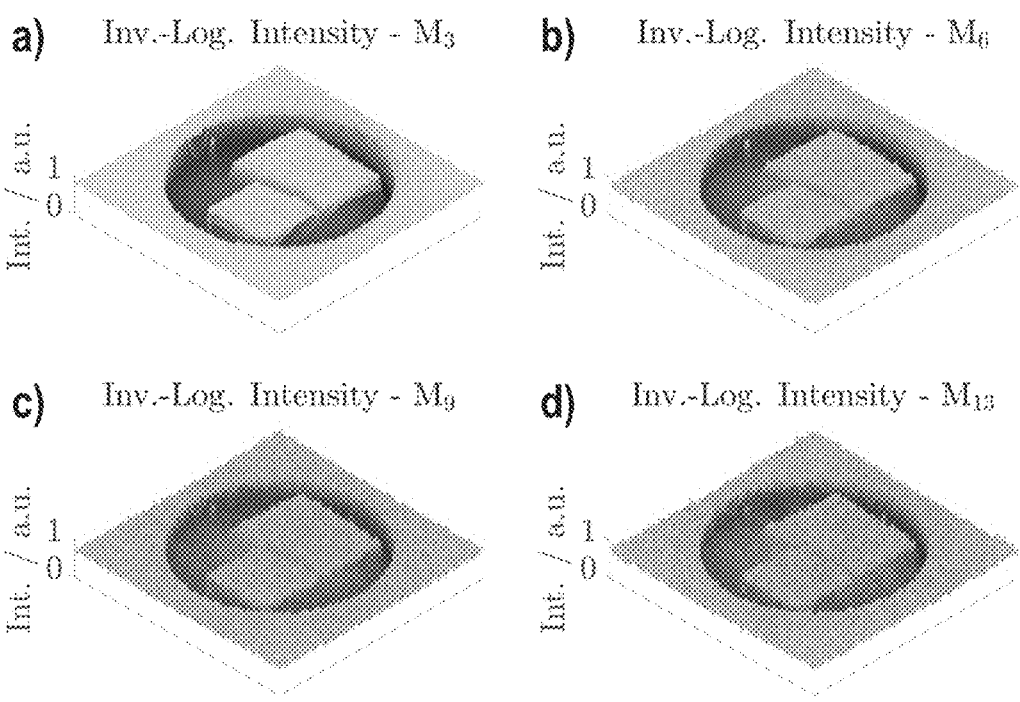
FIG. 11 shows a diagram of the noise behavior in the imaging domain.

The optical impression of low-coherent aliasing artefacts is additionally supported by FIG. 11 which displays the inverse of the logarithmic pixel intensities of all images, shown in FIG. 10. FIG. 11 illustrates the noise behavior in the image domain, illustrated by plotting normalized values of $1-\log(I)$ for all defined undersampling factors $M_3, \ldots, M_{13}$.

The logarithmic visualization explicitly emphasizes artefacts, arising in the background and within the regions inside the phantom, that contain no phantom fluid. Again, a steady increase in pixel intensity variations can be observed, without any obvious coherent aliasing behavior. The representation also nicely highlights the preservation of image sharpness, especially noticeable around the region of no signal within the phantom.

FIG. 12 shows a 3D sketch (FIG. 12*b*) and projections (FIG. 12 *a, c, d*) of the phantom with highlighted region of interest for the noise analysis.

Figure 13:
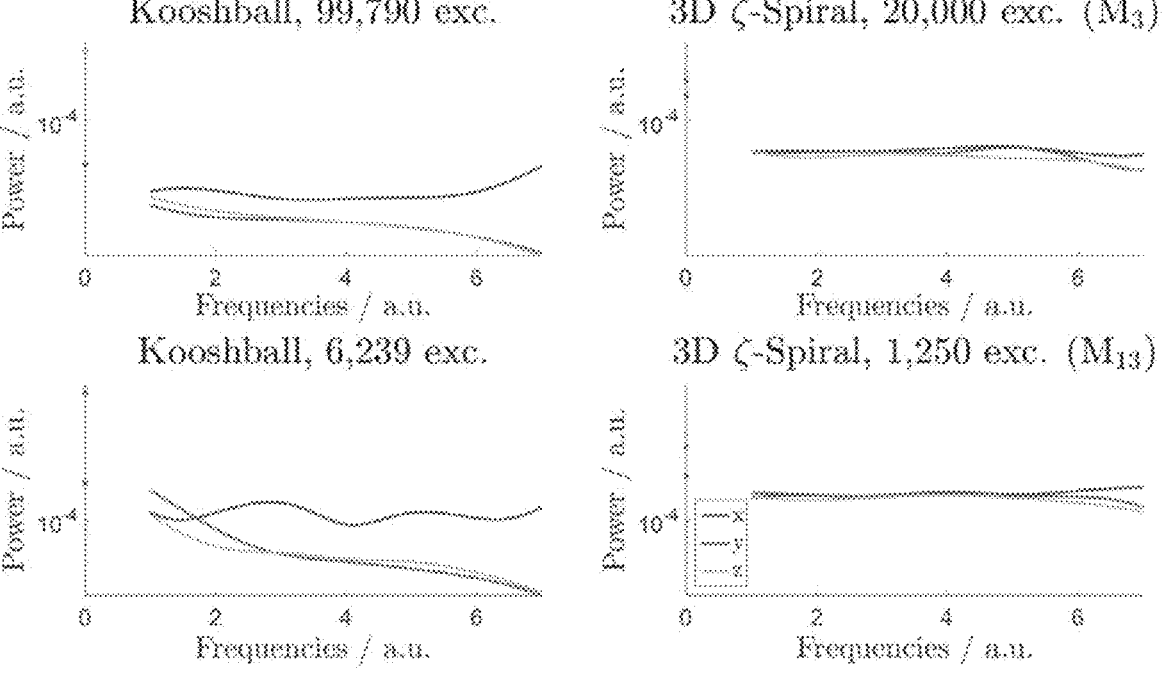
FIG. 13 shows a diagram of normalized power spectra for a region of interest in FIG. 12.

The noise analysis for a cubic region (ROI) inside the phantom is shown in FIG. 13. Therein, FIG. 13 shows normalized power spectra for the cubic region of interest within the phantom, containing no signal. For both trajectories, Kooshball and 3D $\zeta$-Spiral sampling, the lower row is undersampled by a factor of R=16 with respect to the upper row. The normalized power spectra merely indicate slightly overpronounced DC components for all acquisitions. For the 3D $\zeta$-based Spiral trajectories (20,000 and 1,250 interleaves), all further spatial frequency components are about equally represented, leading to a widely flat power spectrum in accordance to the behavior of (bandwidth limited) white noise. As expected, an increasing undersampling factor increases the overall power but the characteristics (line-shapes) remain widely unchanged.

Figure 14:
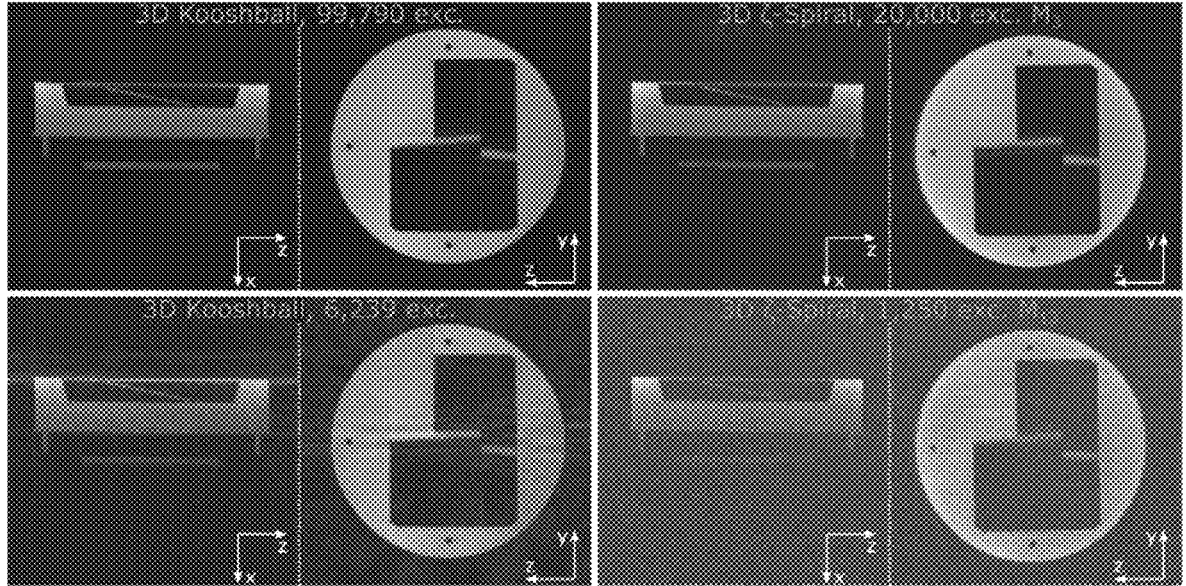
FIG. 14 shows a diagram of image slices based on different acquisition schemes.

Concerning the Kooshball trajectory used for comparison of the performance, the y- and z-components show similar behavior with over pronounced DC components and a following decline of the power spectrum. In the undersampled case, differences between the two directions are a bit more distinct as the z-component exhibits a slight modulation. The x-component also has an over pronounced DC component but further deviates from the behavior of the y- and z-component. It initially shows a rather flat profile but rises for high frequencies. Surprisingly, this behavior is more pronounced in the fully sampled case. However, undersampling may introduce rather strong modulations of the x-component's power spectrum. The findings of this analysis are supported by the visual impression of exemplary image slices given in FIG. 14. While the noise-like characteristics of aliasing artefacts remain unchanged for varying undersampling factors in the case of 3D $\zeta$-based Spiral trajectories, undersampling of the radial Kooshball trajectory introduces streak artefacts.

V. DISCUSSION AND CONCLUSIONS

In summary, all presented experimental results show dominant low-coherent aliasing properties, leading to a noise-like undersampling behavior. The equality between the reconstruction of arbitrary FOVs and the possible violation of Nyquist's theorem leads to new imaging strategies or ways in which available scan times can be exploited.

Beneath obvious advantages in scan time reduction, by a combination of undersampling with a Compressed Sensing reconstruction a variety of new applications and imaging routines seem possible. Using $\zeta$-based spirals, a trajectory might be constructed just by following given time restrictions and imaging constraints, e.g. such as: (1) Size of k-space sphere is defined by the desired image resolution; (2) Maximum read-out duration (spiral length) is defined (limited) by off-resonance behavior and relaxation effects; and (3) Total acceptable scan duration defines the number of possible interleaves.

Based on the measured experimental dataset, any feasible FOV may then be reconstructed by introduction of the presented aliasing artefacts if the condition $\Delta r_C \leq 1/FOV_p$ is not fulfilled for every point in k-space.

Since the reconstructed FOV is typically defined by the underlying Cartesian grid (gridding/interpolation) and not by the trajectory itself, the same Voronoi density compensation can be used for any reconstructed FOV.

The dependence of noise characteristics on the (undersampled) trajectory and the imaged object can especially be appreciated for the Kooshball trajectory. The y- and z-components show very similar behavior, while the x-component behaves differently. This effect is in accordance with the spatial extent of the phantom. For the 3D $\zeta$-based Spiral, no influence of the phantom's symmetry can be seen, due to the favorable aliasing properties of the trajectory.

The presented approach for acquisition of a magnetic resonance image independent of an a-priori defined field-of-view, FOV, in particular based on Jacobi theta functions represents further facilitates acquisition of magnetic resonance images.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

What is claimed is:

1. A method for acquisition of a magnetic resonance image independent of an a-priori defined field-of-view, FOV, the method comprising the sequence of steps:

determining, by a processor, a k-space trajectory for acquisition of k-space MRI data, wherein said k-space trajectory comprises a field-of-view, FOV, independent 3D k-space trajectory, wherein the 3D k-space trajectory for acquisition of the k-space MRI data is independent of an a-priori defined field-of-view of an MRI image to be constructed, wherein said field-of-view-independent 3D k-space trajectory is based on one or more Jacobi theta functions; and wherein one or more of the Jacobi theta functions are provided by at least one of $\theta_1$, $\theta_2$, $\theta_3$, $\theta_4$ wherein $$\theta_1(z, q) := \sum_{n=-\infty}^{\infty} (-1)^{n-1/2} q^{(n+1/2)^2} e^{(2n+1)iz}$$

$$\theta_2(z, q) := \sum_{n=-\infty}^{\infty} q^{(n+1/2)^2} e^{(2n+1)iz}$$

$$\theta_3(z, q) := \sum_{n=-\infty}^{\infty} q^{n^2} e^{2niz}$$

$$\theta_4(z, q) := \sum_{n=-\infty}^{\infty} (-1)^n q^{n^2} e^{2niz},$$

wherein $q \in \mathbb{C}$ and $|q| < 1$, $n \in \mathbb{N}$, acquiring k-space MRI data, wherein a gradient waveform corresponding to said field-of-view independent k-space trajectory is applied to magnetic field gradients of the MRI scanner; and receiving, via a user interface, a selection of a desired field of view for the magnetic resonance image after acquiring the k-space MRI data and constructing the magnetic resonance image based on the desired field of view from the acquired k-space MRI data.

2. The method according to claim 1, wherein said FOV-independent 3D k-space trajectory is determined based on a desired image resolution.

3. The method according to claim 1, wherein said FOV-independent 3D k-space trajectory is determined based on a desired image acquisition time.

4. The method according to claim 1, wherein said a field-of-view independent 3D k-space trajectory is based on a plurality of the Jacobi theta functions, wherein the plurality of Jacobi theta functions are adapted to provide low coherent aliasing properties below a predetermined threshold in the magnetic resonance image.

5. The method according to claim 1, wherein the field-of-view independent 3D k-space trajectory comprises a plurality of different interleaves in k-space based on different Jacobi theta functions.

6. The method according to claim 5, wherein a length of an interleave is determined based on a predetermined read-out time and or resolution.

7. The method according to claim 1, wherein at least one of the Jacobi theta functions is different from a Jacobi elliptic function.

8. The method according to claim 1, adapted to acquire the k-space MRI data by sampling the k-space in a randomized manner.

9. The method according to claim 8, adapted to acquire the k-space MRI data by sampling the-k-space based on one or more Jacobi theta functions.

10. The method according to claim 1, wherein determining the k-space trajectory for acquisition of k-space MRI data comprises retrieving one or more predetermined FOV independent trajectories from a storage of predetermined FOV independent trajectories.

11. A device for determining a trajectory for acquisition of an MRI image, wherein the device is adapted to determine a k-space trajectory for acquisition of k-space MRI data independent of an a-priori defined field of view, FOV, wherein the 3D k-space trajectory for acquisition of the k-space MRI data is independent of an a-priori defined field-of-view of the MRI image; wherein said k-space trajectory comprises a field-of-view independent 3D k-space trajectory based on one or more Jacobi theta functions; and wherein one or more of the Jacobi theta functions are provided by at least one of $\theta_1$, $\theta_2$, $\theta_3$, $\theta_4$, wherein $$\theta_1(z, q) := \sum_{n=-\infty}^{\infty} (-1)^{n-1/2} q^{(n+1/2)^2} e^{(2n+1)iz}$$

$$\theta_2(z, q) := \sum_{n=-\infty}^{\infty} q^{(n+1/2)^2} e^{(2n+1)iz}$$

$$\theta_3(z, q) := \sum_{n=-\infty}^{\infty} q^{n^2} e^{2niz}$$

$$\theta_4(z, q) := \sum_{n=-\infty}^{\infty} (1 - 1)^n q^{n^2} e^{2niz}.$$

wherein $q \in \mathbb{C}$ and $|q| < 1$, $n \in \mathbb{N}$ ..

12. A magnetic resonance imaging system for acquisition of a magnetic resonance image, the system comprising:

a device according to claim 11 for determining a trajectory for acquisition of an MRI image;

an MRI scanner adapted to acquire k-space MRI data, wherein a gradient waveform corresponding to said field-of-view independent k-space trajectory is applied to magnetic field gradients of the MRI scanner; and an image reconstruction device comprising an interface for selecting a desired field of view for the magnetic resonance image after acquiring the k-space MRI data, and adapted to construct the magnetic resonance image based on the desired field of view from the acquired k-space MRI data.

13. A non-transitory computer-readable storage medium comprising program code, which, when executed by a computer, causes the computer to determine a k-space trajectory for acquisition of k-space MRI data independent of an a-priori defined field-of-view, FOV, wherein the 3D k-space trajectory for acquisition of the k-space MRI data is independent of an a-priori defined field-of-view of the MRI image; wherein said k-space trajectory comprises a field-of-view independent 3D k-space trajectory based on one or more Jacobi theta functions; and wherein one or more of the Jacobi theta functions are provided by at least one of $\theta_1$, $\theta_2$, $\theta_3$, $\theta_4$ wherein $$\theta_1(z, q) := \sum_{n=-\infty}^{\infty} (-1)^{n-1/2} q^{(n+1/2)^2} e^{(2n+1)iz} \qquad 5$$

$$\theta_2(z, q) := \sum_{n=-\infty}^{\infty} q^{(n+1/2)^2} e^{(2n+1)iz}$$

$$10$$

$$\theta_3(z, q) := \sum_{n=-\infty}^{\infty} q^{n^2} e^{2niz}$$

$$\theta_4(z, q) := \sum_{n=-\infty}^{\infty} (1-1)^n q^{n^2} e^{2niz}. \qquad 15$$

wherein $q \in \mathbb{C}$ and $|q| < 1$, $n \in \mathbb{N}$.

\* \* \* \* \*